United States Patent [19]
Frechet et al.

[11] Patent Number: 5,522,994
[45] Date of Patent: * Jun. 4, 1996

[54] SINGLE COLUMN CHROMATOGRAPHIC DETERMINATION OF SMALL MOLECULES IN MIXTURES WITH LARGE MOLECULES

[75] Inventors: Jean M. J. Frechet; Frantisek Svec, both of Ithaca, N.Y.

[73] Assignee: Cornell Research Foundation, Inc., Ithaca, N.Y.

[ * ] Notice: The term of this patent shall not extend beyond the expiration date of Pat. No. 5,316,680.

[21] Appl. No.: 384,325

[22] Filed: Feb. 1, 1995

[51] Int. Cl.$^6$ .................................................. B01D 15/08
[52] U.S. Cl. ..................... 210/635; 210/656; 210/198.2; 210/502.1; 530/413; 530/417
[58] Field of Search .................................. 210/635, 656, 210/198.2, 502.1; 502/401, 402, 404; 530/413, 417

[56] References Cited

U.S. PATENT DOCUMENTS

| | | | |
|---|---|---|---|
| 4,000,098 | 12/1976 | Hofstee | 210/198.2 |
| 4,155,846 | 5/1979 | Novak | 210/198.2 |
| 4,160,728 | 7/1979 | Kirkland | 210/198.2 |
| 4,298,500 | 11/1981 | Abbott | 210/198.2 |
| 4,301,139 | 11/1981 | Feingers | 210/198.2 |
| 4,544,485 | 10/1985 | Pinkerton | 210/198.2 |
| 4,699,717 | 10/1987 | Riesner | 210/198.2 |
| 4,740,306 | 4/1988 | Litwack | 210/198.2 |
| 4,778,600 | 10/1988 | Williams | 210/198.2 |
| 4,810,391 | 3/1989 | Bruegger | 210/198.2 |
| 4,941,974 | 7/1990 | Williams | 210/198.2 |
| 4,950,635 | 8/1990 | Williams | 210/198.2 |
| 5,004,547 | 4/1991 | Grunfeld | 210/198.2 |
| 5,110,784 | 5/1992 | Williams | 210/198.2 |
| 5,130,343 | 7/1992 | Frechet | 521/62 |
| 5,133,868 | 7/1992 | Atwood | 210/198.2 |
| 5,137,627 | 8/1992 | Feibush | 210/198.2 |
| 5,316,680 | 5/1994 | Frechet | 210/635 |
| 5,334,310 | 8/1994 | Frechet | 210/198.2 |
| 5,453,185 | 9/1995 | Frechet | 210/198.2 |

OTHER PUBLICATIONS

Wheatly, "Mutiple Ligand, Applications in High–Performance Immunoaffinity Chromatography," Journal of Chromatography, 603 (1992) pp. 273–278.

Little, "Sequential Multimodal Elution for Pseudomultidimensional Liquid Chromatography on a Single Column," Anal. Chem., 63 (1991) pp. 33–34.

Pinkerton, "High–Performance Liquid Chromatography Packing Materials for the Analysis of Small Molecules in Biological Matrices by Direct Injection", Journal of Chromatography, 544 (1991) pp. 13–23.

Haginaka, "Drug Determination in Serum by Liquid Chromatography with Restricted Access Stationary Phases," Trends in Analytical Chemistry, vol. 10, No. 1, 1991, pp. 17–22.

Flory, Principles of Polymer Chemistry, Cornell University Press, 1953, Ithaca, New York, pp. 266–269, 422–425, 594–597, & 606–607.

Primary Examiner—Ernest G. Therkorn
Attorney, Agent, or Firm—Bruce F. Jacobs

[57] ABSTRACT

A process for separating small molecules from a sample containing small and large molecules using a porous separation medium having bimodal chemistry wherein the small molecules are first removed is disclosed.

13 Claims, 1 Drawing Sheet

Time, min

SINGLE COLUMN CHROMATOGRAPHIC DETERMINATION OF SMALL MOLECULES IN MIXTURES WITH LARGE MOLECULES

BACKGROUND OF THE INVENTION

Deproteinization of a sample by precipitation or solvent extraction typically precedes the determination of drugs, endogenous metabolites or other small molecules in physiological liquids by high-performance liquid chromatography. This pretreatment prevents the accumulation of proteins in the column that would likely lead to clogging and fast deterioration of the separation efficiency. However, such pretreatment is time consuming and does not always give reproducible and quantitative results. Therefore, different methods have been developed that allow the direct injection of these complex samples into a chromatograph. The simplest is solid phase extraction (SPE) in which the SPE column is disposed of after each injection. The precolumn technique utilizing two columns in tandem has significant advantages over SPE. Several hundred injections can be made on the precolumn. However, the precolumn technique requires an additional pump, a column switching device and computer control of events.

In parallel, stationary phases based on modified porous silica have been developed to allow the direct injection of complex matrices such as plasma, serum, saliva, and urine into a column for the determination of drugs and metabolites without any pre-treatment (D. J. Anderson, Anal. Chem., 65 (1993) 434R).

The majority of direct injection stationary phases yet described in the literature are based on silica that has been modified in order to prevent the contact of protein molecules with hydrophobic or charged functionalities attached to surface of the stationary phase (Pinkerton U.S. Pat. No. 4,544,485). In each case, the modification of the pores is uniform and affects all pores regardless of their size. Moreover, some of these silica based packings have limited working pH range, ionic strength range, or do not allow any high concentrations of organic solvent in the mobile phase during the reversed phase chromatography. The modifications may also impair diffusion of the low molecular weight compounds that have to be separated, and the slow mass transfer results in lower column efficiencies (about 20–36, 000 plates/m) when compared to those of typical reversed phase silica columns.

Polymeric stationary phases have gained considerable popularity in HPLC due to their chemical stability in the entire pH range, broad variety of available surface groups chemistries and polarities. Styrene-divinylbenzene copolymers are the most often used polymeric stationary phases. Their highly hydrophobic surface accounts for their extensive use in reversed-phase chromatography and size-exclusion chromatography in non-aqueous media. A search for more hydrophilic stationary phases is still in progress in order to develop polymeric media for the separation of water soluble hydrophilic compounds and proteins without damaging their biological activity. Though more rugged in terms of chemical resistance, the polymeric stationary phases are essentially less efficient than silica based phases with efficiencies seldom exceeding 30,000 plates/m. Despite this limitation, the ability to modify the chemistry within specialized polymer phases remains a very significant advantage that frequently justifies their use. Recently, a few stationary phases for direct injection chromatography of complex samples based entirely on organic polymers were described in the literature (Hosoya et al., *Chromatographia* 38 (1994) 177; Beth et al. (*Chromatographia* 36 (1993) 351; Smigol et al, *J. Liquid Chromatog.* 17 (1994) 891).

The chromatographic method used for all of the separation media for direct injection chromatography is essentially the same. The sample that typically contains large protein molecules and small hydrophobic molecules (drugs, metabolites, etc.) is injected into the packed column and eluted with a mobile phase consisting of an aqueous buffer solution and an organic solvent. Due to the design of the separation media, the proteins are not retained within the column and elute in the void volume. In contrast, small more hydrophobic molecules are retained in the separation medium and elute after the proteins in an order that reflects their hydrophobicity. The typical drawback of such a direct injection separation technique is that the peak of the proteins typically has a long tail and less hydrophobic small molecules elute before the major peak reaches the baseline. This has an impact on the accuracy of the quantitative determination of small molecule drugs.

A far better approach would be to separate the small molecules first while the proteins remain completely retained on the top of the column and are released only by a different mobile phase at the end of the chromatographic run. Accordingly, it is an object of the present invention to achieve the complete separation of small molecules in complex samples using a technique that is inverse to the techniques of the prior art.

SUMMARY OF THE INVENTION

Accordingly, the present invention is directed to a process for separating molecules from complex samples in a single column packed with a packing material that has two different types of functionalities with each different of functionality segregated in pores of different sizes. Thus, for example, pores within one pore size range will have one type of functionality and pores within a different pore size range will have a different functionality.

The process comprises (1) adding a sample that contains at least two different size molecules to a device that contains a porous separation medium having at least two different types of functionalites with each different type of functionality segregated in pores of different sizes, (2) separating the smaller molecules contained in the sample by eluting them with a first mobile phase leaving the larger molecules sorbed in the porous medium, and (3) thereafter eluting the larger molecules by washing the sample and porous separation medium with a different mobile phase. This process may contain multiple steps whereby molecules of different sizes are separated in a series of mobile phase washings using a different mobile phase for each different group of molecules. In such case, separation will take place according to the polarity of the small molecules so that all the small molecules in one set are removed followed by another set of small molecules. The selection of the particular mobile phase will depend on the chemistry of the small molecules and the chemistry of the porous medium being used. After each washing, the large molecules in the sample remain adhered to the porous separation medium in its larger pores. While this process can be used with any sample containing small and large molecules, it is particularly useful in separating small molecules such as drugs from large molecules such as proteins, like those contained in blood plasma or serum, and polymers. As used herein, small molecules generally have a molecular weight of less than about 1000 and large molecules generally have a molecular weight that exceeds that value. The large pores of the porous separation medium are provided with a chemistry that enables them to interact with the larger molecules such as proteins and bind them temporarily. The small molecules can penetrate the small pores provided with a different chemistry and are separated according to their polarity. During this separation, the large molecules remain absorbed in the column. After the separation of the small molecules of interest is completed, the composition of the mobile phase is changed and the proteins eluted. This "clean up" step must be followed by the washing with the original mobile phase, that again allows the selective binding of large molecules and the separation of small ones, when the next sample to be injected has to be separated under the condition of the previous separation. Otherwise, this clean-up mobile phase may be different but still suitable for analysis.

The device used to carry out the process of the present invention is preferably a conventional chromatographic separation column, but may be any suitable device to effect the desired separation.

DETAILED DESCRIPTION OF THE PREFERRED EMBODIMENT(S)

Figure 1:
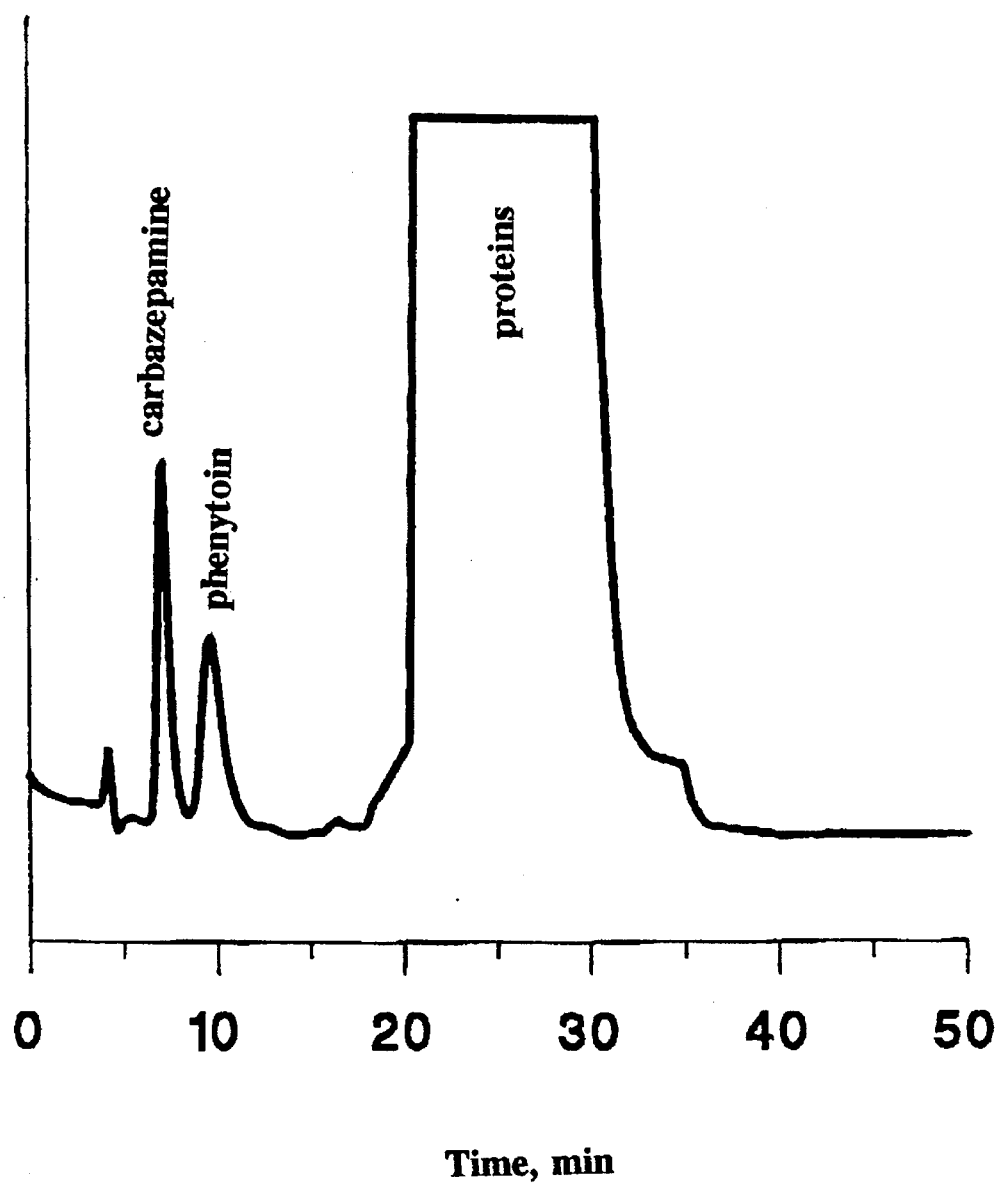
FIG. 1 is the chromatogram resulting from the Example.

In the process of the present invention, the mobile phase used to separate the small molecules from the porous separation medium will, as explained previously, depend on the polarity of the small molecules to be separated. Suitable mobile phases to effect such separation generally contain a mixture of an aqueous buffer solution with low ionic strength; eg., an ionic strength of from about 0.001 to 0.01 mol/L, and up to 50% of an organic solvent. Suitable aqueous buffer solutions include, for example, phosphate, borate, acetate, TRIS-HCl and glycinate. Suitable solvents include tetrahydrofuran, acetonitrile, methanol and propanol.

After separation of the small molecules, the large molecules which remain in the large pores of the separation medium are separated using a suitable eluting media such as buffered solutions of inorganic salts like sodium chloride, potassium chloride and ammonium sulfate in a concentration of from about 0.5 to 2.5 mol/L.

The packing material used to pack the chromatographic column used in the present invention must be a porous material having bimodal chemistry; i.e. at least two different types of functionality segregated in pores of different sizes.

The separation according to the present invention cannot be achieved with the common separation media. Even if two different separation media, each one provided with one of the chemistries accomodated in the dual chemistry beads, would be blended, the separation of a complex sample would not be possible. For example, a blend of ion-exchange beads and hydrophobic reversed-phase separation medium would operate for a very limited number of assays because the "clean-up" procedure typical for the present invention is not able to remove the proteins adsorbed on the surface of the hydrophobic medium. The proteins will accumulate there and deteriorate the separation ability of the beads very quickly.

The separation according to the present invention also cannot be achieved with the more conventional media used for direct injection chromatography. These media are designed in such a way that the proteins must not be sorbed in any suitable mobile phase. Therefore, the peak of proteins precedes the peaks of the small molecules with the consequence of an incomplete separation of the less retained hydrophobic compounds. The particular bimodal chemistry may be designed to effect the desired separation. The presently preferred process for making such porous separation media generally comprises treating a porous material having reactive groups within its pores with a modifying agent of a size which penetrates into only certain pores of the porous material, which modifying agent chemically modifies or assists in the chemical modification of the reactive groups only within the pores so penetrated. The porous material may have a variety of different pore sizes generally ranging from about 1 to 1500 nm. The surfaces of the pores have surface groups which are reactive groups such as epoxy, alcohol, acetal, aldehyde, chloromethyl, thiol, amine, ester, carboxylic acid and anhydride, amide, oxime, imine, hydrazone, enamine, or oxazoline groups. The reactive groups within the pores determine the reactivity of the surfaces thereof.

The process selectively modifies the pores of the porous material by employing a modifying agent which reacts with the reactive groups in the pores, or catalyzes their reaction with another reagent, to chemically modify the reactive surface groups to different surface groups, thereby changing the surface functionality of the pore surface. For example, hydrophilic reactive groups can be changed to hydrophobic groups and vice-versa, changing the surface functionality of the pore surface.

Selective modification is achieved by using a modifying agent such as a catalyst or reagent which is of a size which permits it to penetrate into only certain sized pores. Once it penetrates into the pores in which it fits, the chemical modification occurs transforming the reactive groups therein to surface groups of a different functionality than the original reactive groups. The pores into which the modifying agent can not penetrate because of size constraints remain unmodified. The resultant porous material contains pores with different surface functionalities.

The process also includes the preparation of materials possessing different reactive groups in pores of different sizes by a series of consecutive reactions using modifying agents with different molecular sizes. In this way, a porous material may be produced containing two or more different surface functionalities localized in pores of different sizes. For example, the porous material may be first modified using a relatively low molecular volume modifying agent which transforms all accessible groups in substantially all of the pores from one functionality to another functionality, and then another modifying agent with a larger molecular volume than the first modifying agent is used to penetrate only relatively larger pores, thereby changing the functionality therein. In a consecutive fashion, modifying agents each having relatively larger molecular volumes than the last one employed may be used to change the functionalities only in the pores in which they fit. While this convergent process may employ an unlimited number of different size modifying agents, generally from about 2 to 5 and more preferably from about 2 to 3 different size modifying agents are used. The resultant porous material generally contains pores with about 2 to 5 and more preferably from about 2 to 3 different functionalities. The convergent process can be reversed by starting with a relatively large modifying agent and gradually decreasing the size of the modifying agent in each divergent process step. Alternatively the convergent and divergent process can be combined using, for example, a relatively small molecular volume catalyst in the first reaction step, a relatively large molecular volume catalyst in the second reaction step and modifying agents with molecular volumes therebetween the two used in the first two step in remaining steps. The process variants depend on the porous material, modifying agent, reactive groups and desired product.

The products so produced comprise porous materials having at least two different pore size ranges, with the pores of one size range having surface groups of one functionality and the pores of another size range having surface groups of a different functionality. For example, pores within the range of 1 up to 5 nm may have hydrophilic groups and pores within the range of more than 5 to 50 nm may have hydrophobic groups. Numerous other combinations are possible.

The selection of the porous material and the modifying agent will depend on the desired result. Thus, the porous material may be selected so that it has hydrophobic groups in its pores, which groups can be changed by the modifying agent to be hydrophilic groups in all but the smallest pores. Alternatively, the porous material may be selected so that it has hydrophilic groups within its pores, which can be changed by the modifying agent to be hydrophobic groups in all but certain sized pores. In conjunction with choosing the porous material, the modifying agent must also be chosen to produce a certain result. The modifying agent must be chosen so that it is capable of reacting with, or catalyzing, the reaction of the reactive groups in the pores of the porous material. Relatively large (molecular size) modifying agents may be used in situations wherein it is desired to only modify the surface characteristics of the larger pores in the porous material. Alternatively, a relatively small modifying agent may be used in situations wherein it is desired to modify the majority of the pores in the porous material. The degree of chemical modification and the size of pores modified can, by this preselection technique, be controlled to produce a predesigned porous material intended for a particular end use.

A large variety of porous materials may be employed in the process. Suitable porous materials include macroporous polymers such as polymers of glycidyl methacrylate or acrylate; 2-hydroxyethyl methacrylate or acrylate; allyl methacrylate or acrylate; chloromethylstyrene; 4-tert-butoxycarbonyloxystyrene; vinylacetate; vinylacetals; vinyl alcohol, vinylbenzyl alcohol or vinyl phenol and esters or ethers thereof; 4-nitrophenyl acrylate; 2,4,5-tri-chlorophenyl acrylate; acryloyl succinimide; maleic acid; vinylbenzaldehyde, acrolein, or methacrolein or acetal, imine, oxime, or hydrazone derivatives thereof; crosslinked with any of divinylbenzene; ethylene dimethacrylate or acrylate; diethylene glycol methacrylate or acrylate; divinylpyridine; bis-N-vinyl- 2-pyrrolidone; N,N-methylene-bis-acrylamide; or trimethylolpropane trimethacrylate. Other suitable porous materials are based on natural polysaccharides such as cellulose, chitin, agarose, guar, and dextran. The porous material may also be an inorganic oxide such as silica, titania, zirconia, alumina, magnesia, and porous glass. Other suitable porous materials include bonded reactive phase materials prepared by the reaction of an inorganic oxide with a reactive silylation agent such as 1-glycidoxypropyltrimethoxysilane, vinyltrimethoxysilane, and other silanes. The medium pore size of such porous materials is from about 2 to about 100 nm. The pore size distribution generally ranges from about 1 to about 1500 nm. The porous material may be of any suitable shape such as beaded (spherical), irregular, rod shaped, flat membrane-like or any other continuous shape. These porous materials are either commercially available from sources such as Rohm and Haas, Mitsubishi, Dow, Bio-Rad, and Merck, or may be prepared by techniques known in the art such as disclosed in U.S. Pat. No. 5,130,343, which is incorporated herein by reference.

Each porous material contains particular reactive groups within its pores. Depending upon the porous material, the reactive groups can include epoxy, alcohol, acetal, aldehyde, chloromethyl, thiol, amine, ester, carbonate, carboxylic acid, amide, oxime, imine, hydrazone, enamine, oxazoline or carboxylic anhydride groups. The reactive groups will determine which modifying agents need to be used to modify the reactive groups to obtain the desired surface functionality of the pores in the porous material. The final surface functionality depends on the reaction scheme used to produce the final surface groups and to a lesser extent the initial surface groups. Example of suitable reaction schemes are disclosed hereinafter. Surface groups according to the present invention may have functionalities that include hydrophobic, hydrophilic, anion-exchange, cation-exchange, affinity, charge transfer, catalytic and metal ion complexing.

The modifying agents are selected by their size and ability to react with or catalyze the modification of reactive groups in the pores of the porous material. The size of the modifying agent is selected based on the pore sizes of the porous material containing reactive groups to be modified. Suitable modifying agents for larger pores, e.g. greater than about 10 nm, include polymeric catalysts such as poly(styrenesulfonic acid), poly(methacrylic acid), poly(acrylic acid), poly(vinylbenzoic acid), or a peracid thereof; poly(ethyleneimine) and its quaternized derivatives, poly(triethylaminoethyl methacrylate), polyvinylpyridine and its quaternized derivatives, or poly(trimethylaminomethylstyrene) and polymeric reagents including a polymeric carbodimide or similar polymeric coupling agent; a polymeric dimethylaminopyridine or similar acylation agent, polymeric amine or other polymers containing basic substituents. Suitable modifying agents for smaller pores, e.g. about 1 to about 10 nm, include such as sulfuric acid, sodium hydroxide, triethylamine, dimethylaminopyridine. The small pore agents will be capable of modifying not only the small pores but also the large pores.

It is well known that the size of a polymer molecule in solution or its hydrodynamic volume, i.e. the volume it occupies in solution, varies with its molecular weight and with the solvent used. (P. J. Flory, Principles of Polymer Chemistry, Cornell University Press, 1953); (G. Allen and J. Bevington, Eds., Comprehensive Polymer Science, Pergamon Press, 1989, Volume 2, p. 199).

In the case of the reagent, the reagent reacts with the reactive groups in the pores of the porous material into which it enters to change them chemically into different surface groups. The catalyst on the other hand functions by catalyzing the reaction of the reactive groups with a reagent present in the pores. For example, if the surface of the pores contain reactive epoxy groups and if the catalyst is a polymeric acid in water, the epoxy groups will react with water in a hydrolysis reaction that will transform the epoxy groups into diol groups only when the catalyst is present. In the areas where the polymeric acid catalyst is not present (small pores because of size constraints), the epoxy groups will not react with water since the hydrolysis reaction cannot occur in the absence of the catalyst. After the modification of the desired pores is finished, the catalyst is washed out of the pores and may be reused for a subsequent modification.

More specific examples of the production of the bimodal separation media useful in the process of the present invention are described in U.S. Pat. No. 5,316,680, which is incorporated herein by reference.

The present invention will now be described with reference to the following non-limiting Example in which all parts and percents are by weight unless otherwise specified.

EXAMPLE

The separation media that contains strictly segregated diethylaminohydroxypropyl functionalities in large pores and octadecyl functionalities in small pores was prepared in accordance with the procedure described in U.S. Pat. No. 5,316,680. Specifically, the hydrolysis of the poly(glycidyl methacrylate-co-ethylene dimethacrylate) resin containing epoxide groups was catalyzed with 1 wt. % aqueous solution of poly(styrenesulfonic acid) MW5 000 containing 0.054 mol/L sulfonic groups. The epoxide resin (1.6 g) was placed in a 50 mL beaker, 10 mL of aqueous catalyst solution was added and the beaker sealed with Parafilm. The dispersion was stirred magnetically at ambient temperature for 48 hours. The resulting beads were then filtered off on a fritted glass filter and washed with water until neutral, washed with acetone, and dried in vacuo at room temperature.

The beads containing both vicinal hydroxyl groups in large pores and residual epoxide groups in small pores were admixed to 5 g molten octadecylamine in a 50-mL round bottom flask at 70° C. and the mixture was stirred for 16 hours. The reaction mixture was then diluted with 20 mL 1,4-dioxane, stirred for 30 minutes and filtered. The resulting beads were washed with dioxane and water. Any unreacted epoxide groups remaining due to steric constrains were hydrolyzed in 20 mL 0.1 mol/L sulfuric acid at 60° C. for 4 hours. The beads were filtered, washed with water, then with methanol and dried. The amino groups content of the beads was 0.35 mmol/g as determined by elemental analysis of nitrogen as well as by an acid-base titration.

Dry beads from the previous reaction step were dispersed in 20 mL water and stirred magnetically for 16 h. The excess water was removed on a fritted glass filter and the beads redispersed in 20 mL 50 wt. % aqueous KOH and stirred for 1 hr. After removal of the liquid, the beads were added to 40 ml of an epichlorohydrin-water (1:1) mixture and stirred at room temperature for 3 h. The product was washed with water and acetone and dried to afford beads containing epoxide functionalities in the large pores only (1.12 mmol/g epoxide groups determined by volumetric titration).

The epoxidized beads were placed in a 50-mL round bottom flask and 20 mL diethylamine was added. After heating at reflux (55° C.) for 6 hours, the resin was filtered and washed with water. Any remaining unreacted epoxide groups were again hydrolyzed in 20 mL 0.1 mol/L sulfuric acid at 60° C. for 4 hours. Finally, the beads were filtered, washed with water, then with methanol and dried. The beads contained 0.62 mmol/g diethylaminohydroxypropl groups, as determined by elemental analysis of nitrogen after subtraction of the nitrogen introduced with octadecylamino groups.

A liquid chromatographic column 100 mm long and 8 mm in diameter was packed with the modified beads in a flow of water under a constant pressure of 10 MPa and the column was attached to a Waters HPLC chromatograph. The peaks were monitored at 254 nm.

An artificial sample (20 µL) used to mimic human blood plasma comprising a solution of bovine plasma (70 mg/mL) and anticonvulsant drugs carbazepamine (8 µg/mL) and phenytoin (40 µg/ml) was injected into the column. The column was first eluted with a 20:80 vol. % mixture of 0.01 mol/L TRIS-HCl buffer solution (pH 7.6) and acetonitrile at a flow rate of 1 mL/min. As seen in the chromatogram of FIG. 1, the drugs were baseline separated within 10 min without any interference of the plasma proteins. The proteins remained adsorbed by an ion-exchange mechanism in the large pores during this separation. After 15 minutes of elution with the acetonitrile containing mobile phase, the mobile phase was changed to water for 2 minutes followed by 1 mol/L sodium chloride solution in the 0.01 TRIS-HCl buffer and the adsorbed protein released as a single large peak. After the clean-up with sodium chloride solution, the column was washed for 2 minutes with water and for 3 minutes with the acetonitrile containing mobile phase. When the washing procedure was completed, the column was ready for the next injection.

What we claim is:

1. A process for separating molecules of at least two different sizes from a sample containing such comprising the steps of (1) adding a sample that contains at least two different size molecules to a device that contains a porous separation medium having at least two different types of functionalites with each different type of functionality segregated in pores of different sizes, (2) separating the smaller molecules contained in the sample by eluting them with a first mobile phase leaving the larger molecules sorbed in the porous medium, and (3) thereafter eluting the largest of molecules by washing the porous separation medium with a different mobile phase.

2. The process of claim 1, wherein the small molecules are hydrophobic.

3. The process of claim 2, wherein the small molecules are drugs.

4. The process of claim 1, wherein the large molecules are polymers.

5. The process of claim 1, wherein the large molecules are proteins.

6. The process of claim 1, wherein the sample is blood plasma or serum containing small molecules.

7. The process of claim 1, wherein the device is a column containing the porous separation medium.

8. The process of claim 7, wherein the column is packed with porous beads.

9. The process of claim 1, wherein the device is a continuous porous rod.

10. The process of claim 1, wherein the porous separation medium has large and small pores and contains ion-exchange chemistry in large pores and reversed-phase chemistry in small pores.

11. The process of claim 1, wherein the mobile phases used in steps (2) and (3) are mixtures of at least two components.

12. The process of claim 11, wherein the mobile phase for elution of small molecules is a mixture of acetonitrile and an aqueous buffer.

13. The process of claim 11, wherein the mobile phase for elution of large molecules is an aqueous buffer that contains dissolved salt.

* * * * *

UNITED STATES PATENT AND TRADEMARK OFFICE
CERTIFICATE OF CORRECTION

PATENT NO.   : 5,522,994
DATED        : June 4, 1996
INVENTOR(S)  : FRECHET ET AL It is certified that error appears in the above-indentified patent and that said Letters Patent is hereby corrected as shown below:

Column 1, line 5,

> This invention was made with government support under Grant No. A58-8304 awarded by the National Institutes of Health. The government has certain rights in the invention.

Signed and Sealed this

Twelfth Day of November, 1996

Attest:

BRUCE LEHMAN

*Attesting Officer*    *Commissioner of Patents and Trademarks*